(12) United States Patent
Al-Jarba

(10) Patent No.: US 10,052,169 B2
(45) Date of Patent: Aug. 21, 2018

(54) SHIELD FOR ELECTROSURGICAL SUCTION COAGULATOR AND KIT INCLUDING THE SAME

(71) Applicant: Meshil A. M. O. H. Al-Jarba, Safat (KW)

(72) Inventor: Meshil A. M. O. H. Al-Jarba, Safat (KW)

( * ) Notice: Subject to any disclaimer, the term of this patent is extended or adjusted under 35 U.S.C. 154(b) by 0 days.

(21) Appl. No.: 15/788,151

(22) Filed: Oct. 19, 2017

(65) Prior Publication Data
US 2018/0116750 A1 May 3, 2018

Related U.S. Application Data

(60) Provisional application No. 62/417,256, filed on Nov. 3, 2016.

(51) Int. Cl.
*A61B 90/00* (2016.01)
*A61B 18/14* (2006.01)
*A61B 18/00* (2006.01)

(52) U.S. Cl.
CPC ............ *A61B 90/04* (2016.02); *A61B 18/148* (2013.01); *A61B 2018/00083* (2013.01); *A61B 2018/00101* (2013.01); *A61B 2018/00589* (2013.01); *A61B 2090/0436* (2016.02); *A61B 2090/0481* (2016.02); *A61B 2218/007* (2013.01)

(58) Field of Classification Search
CPC ............ A61B 90/04; A61B 2090/0481; A61B 2090/0436
See application file for complete search history.

(56) References Cited

U.S. PATENT DOCUMENTS

| 4,362,160 A | 12/1982 | Hiltebrandt | |
|---|---|---|---|
| 4,719,914 A * | 1/1988 | Johnson | A61B 18/082 604/35 |
| 4,949,734 A * | 8/1990 | Bernstein | A61B 90/05 128/897 |
| 5,089,002 A | 2/1992 | Kirwan | |
| 5,234,428 A * | 8/1993 | Kaufman | A61B 18/1402 604/35 |

(Continued)

FOREIGN PATENT DOCUMENTS

| FR | 2725891 A1 * | 4/1996 | ............. A61B 17/24 |
|---|---|---|---|
| WO | 0028908 A1 | 5/2000 | |

*Primary Examiner* — Lee S Cohen
*Assistant Examiner* — Ryan T Clark
(74) *Attorney, Agent, or Firm* — Richard C. Litman

(57) ABSTRACT

The shield for an electrosurgical suction coagulator includes a cylindrical cuff and a shielding portion. The cylindrical cuff is sized for releasably engaging a distal end of a shaft of an electrosurgical suction coagulator. The shielding portion has an arcuate cross-sectional contour and is mounted on the cylindrical cuff such that the shielding portion extends distally therefrom. The shielding portion has a radius of curvature equal to a radius of curvature of the cylindrical cuff and is positioned coaxially therewith. A plurality of shields for the electrosurgical suction coagulator may be provided in a kit, along with the electrosurgical suction coagulator. In the kit, a circumferential length of each shielding portion of each shield is unique, such that a user of the electrosurgical suction coagulator may select a desired one of the shields for a desired amount of shielding coverage.

3 Claims, 3 Drawing Sheets

(56) References Cited

U.S. PATENT DOCUMENTS

| | | | | |
|---|---|---|---|---|
| 5,738,679 | A | * | 4/1998 | Daikuzono .......... A61B 18/203 606/11 |
| 5,759,150 | A | * | 6/1998 | Konou ............. A61B 17/00008 600/114 |
| 6,142,995 | A | * | 11/2000 | Cosmescu ............ A61B 18/042 604/34 |
| 7,066,875 | B2 | | 6/2006 | Knighton et al. |
| 8,753,341 | B2 | | 6/2014 | Landry et al. |
| 9,028,490 | B2 | | 5/2015 | Heard et al. |
| 2005/0124988 | A1 | * | 6/2005 | Terrill-Grisoni ... A61B 17/3403 606/53 |
| 2005/0131399 | A1 | * | 6/2005 | Loeb ....................... A61B 18/24 606/15 |
| 2005/0234477 | A1 | * | 10/2005 | Brown ................... A61B 17/54 606/131 |
| 2007/0167775 | A1 | * | 7/2007 | Kochavi .............. A61B 5/6885 600/439 |
| 2008/0009659 | A1 | * | 1/2008 | Smith .................. A61N 5/1015 600/3 |
| 2012/0232339 | A1 | * | 9/2012 | Csiky .................. H05K 999/99 600/104 |
| 2013/0231528 | A1 | * | 9/2013 | Voic ............... A61B 17/320068 600/104 |
| 2013/0317529 | A1 | * | 11/2013 | Golden ............. A61B 10/0275 606/159 |
| 2014/0088577 | A1 | * | 3/2014 | Anastassiou ......... A61B 18/201 606/17 |
| 2015/0005761 | A1 | | 1/2015 | Zinnanti |
| 2016/0193006 | A1 | | 7/2016 | Azoulay |

* cited by examiner

SHIELD FOR ELECTROSURGICAL SUCTION COAGULATOR AND KIT INCLUDING THE SAME

CROSS-REFERENCE TO RELATED APPLICATION

This application claims the benefit of U.S. Provisional Patent Application Ser. No. 62/417,256, filed on Nov. 3, 2016.

BACKGROUND

1. Field

The disclosure of the present patent application relates to electrosurgical instruments, and particularly, to a shield for an electrosurgical suction coagulator for the prevention of damage to adjacent tissue during a surgical procedure.

2. Description of the Related Art

The coagulation of bleeding blood vessels and tissue using electrically conductive suction tubes is a technique which is widely used in surgery. Typically, a combination electrosurgery and suction device is employed in surgery wherever excessive blood must be removed from the bleeding site in order to facilitate hemostasis of any bleeding vessels. During any given surgical procedure, several layers of tissue usually must be penetrated to reach the operative field. When resecting an organ, such as a gallbladder, for example, the tissue surrounding the organ must be penetrated and dissected before the organ can be removed. The tissues being dissected, however, often contain blood vessels, nerves, lymph vessels and the like, which should not be severed. The technique of blunt dissection is often used to prevent unnecessary damage caused by severing these vessels or nerves.

The use of electrical energy including radiofrequency and microwave energy and, in particular, radiofrequency (RF) electrodes or microwave antennae for ablation of tissue in the body or for the treatment of pain is well known. For example, electrosurgery is the technique of using alternating current electrical signals in the approximately 200 kHz-3.3 mHz range that are generated by a source of electrosurgical energy, such as an electrosurgical generator, in connection with surgical instruments, to cut or coagulate biologic tissue endogenically.

The electrosurgical signal is applied to the patient via electrodes in either monopolar mode or bipolar mode. In monopolar mode, the active electrode is the surgical instrument at the surgical site, and the return electrode is elsewhere on the patient, such that the electrosurgical signal passes through the patient's body from the surgical site to the return electrode. In bipolar mode, both the active and return electrodes are at the surgical site, such as with an instrument having an array of electrodes, so that the electrosurgical signal passes only through the tissue situated between the RF electrodes of the instrument.

Electrosurgical suction coagulators, which both coagulate and dissect tissue, have also been available for some time. Generally, these devices include a shaft formed from a conductive suction tube electrode having an electrically insulating coating over all but a most distal portion of the tube, so that the distal portion forms a generally annular ablating electrode. The shaft may be formed of malleable materials to enable a surgeon to bend the shaft to a desired shape. The distal end can be used as a blunt dissection device and/or a blunt coagulator. A suction source is attached to a proximal portion of the tube for evacuating excess fluid and debris from the surgical site through the distal end of the tube. The electrode is operably coupled to a source of electrosurgical energy, such as an electrosurgical generator.

FIG. 2 illustrates an example of a conventional or typical electrosurgical suction coagulator 100. As shown, electrosurgical suction coagulator 100 includes a suction coagulator 110 that is operably coupled to an electrosurgical generator 140 via a cable 145. Suction coagulator 110 is operably coupled to a vacuum source 150 by a lumen 155. The suction coagulator 110 includes a handle 115 disposed at the proximal end thereof and an elongated shaft 120 extending distally from the handle 115. The shaft 120 is typically formed from material having malleable or flexible properties, such as aluminum and/or polymeric materials, allowing shaft 120 to be bent to a desired shape by the surgeon, as shown in dashed lines in FIG. 2.

The distal end 124 of shaft 120 includes an exposed tubular electrode 125 for delivering electrosurgical energy to tissue. The electrode 125 has a conduit 126 defined longitudinally therethrough for providing suction to a surgical site. Conduit 126 is in fluid communication with vacuum source 150 via lumen 155. Unfortunately, because the tubular electrode 125 in such typical systems is fully exposed, the electrosurgical energy may be delivered to the surrounding tissue, thus creating unintended damage to healthy tissue surrounding the surgical site. Thus, a shield for an electrosurgical suction coagulator solving the aforementioned problems is desired.

SUMMARY

The shield for an electrosurgical suction coagulator includes a cylindrical cuff and a shielding portion. The cylindrical cuff is sized for releasably engaging a distal end of a shaft of an electrosurgical suction coagulator. The shielding portion has an arcuate cross-sectional contour and is mounted on the cylindrical cuff such that the shielding portion extends distally therefrom. The shielding portion has a radius of curvature equal to a radius of curvature of the cylindrical cuff and is positioned coaxially therewith. When the electrosurgical suction coagulator is in use on a patient's tissue, the shielding portion prevents damage to adjacent tissue.

A plurality of shields for the electrosurgical suction coagulator may be provided in a kit, along with the electrosurgical suction coagulator. In the kit, a circumferential length of each shielding portion of each shield is unique, such that a user of the electrosurgical suction coagulator may select a desired one of the shields for a desired amount of shielding coverage.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
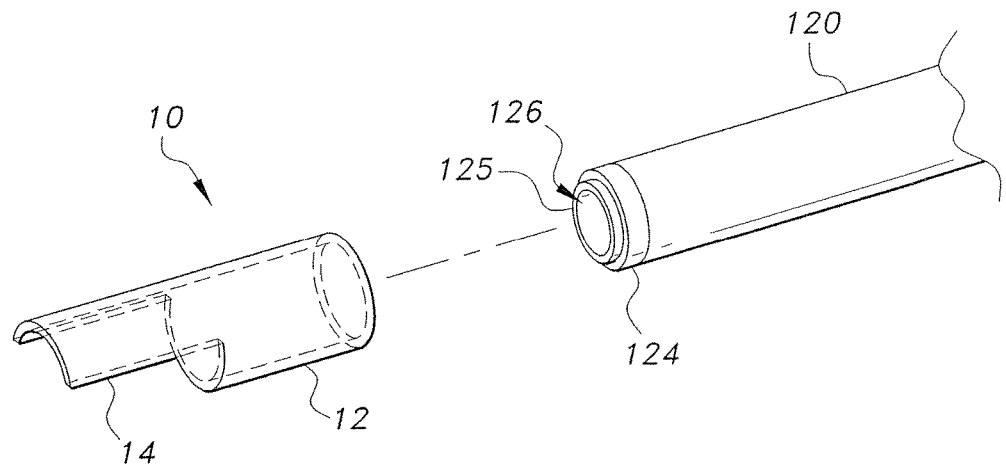
FIG. 1A is a perspective view of a shield for an electrosurgical suction coagulator.
Figure 1B:
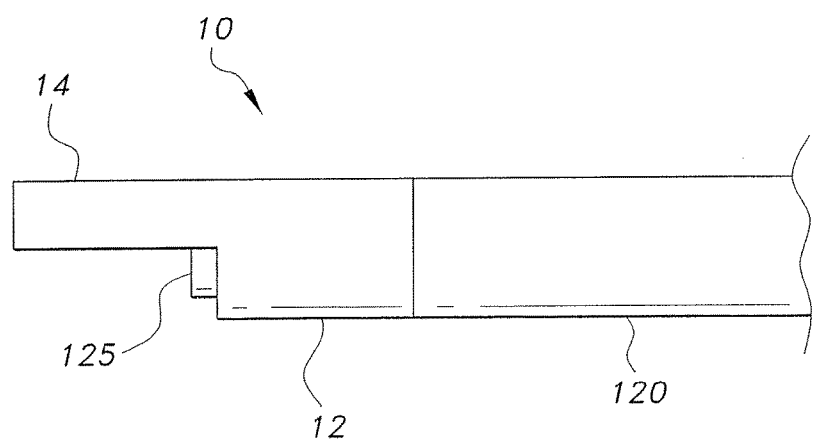
FIG. 1B is a side view of the shield of FIG. 1 mounted on an exemplary prior art electrosurgical suction coagulator.
Figure 2:
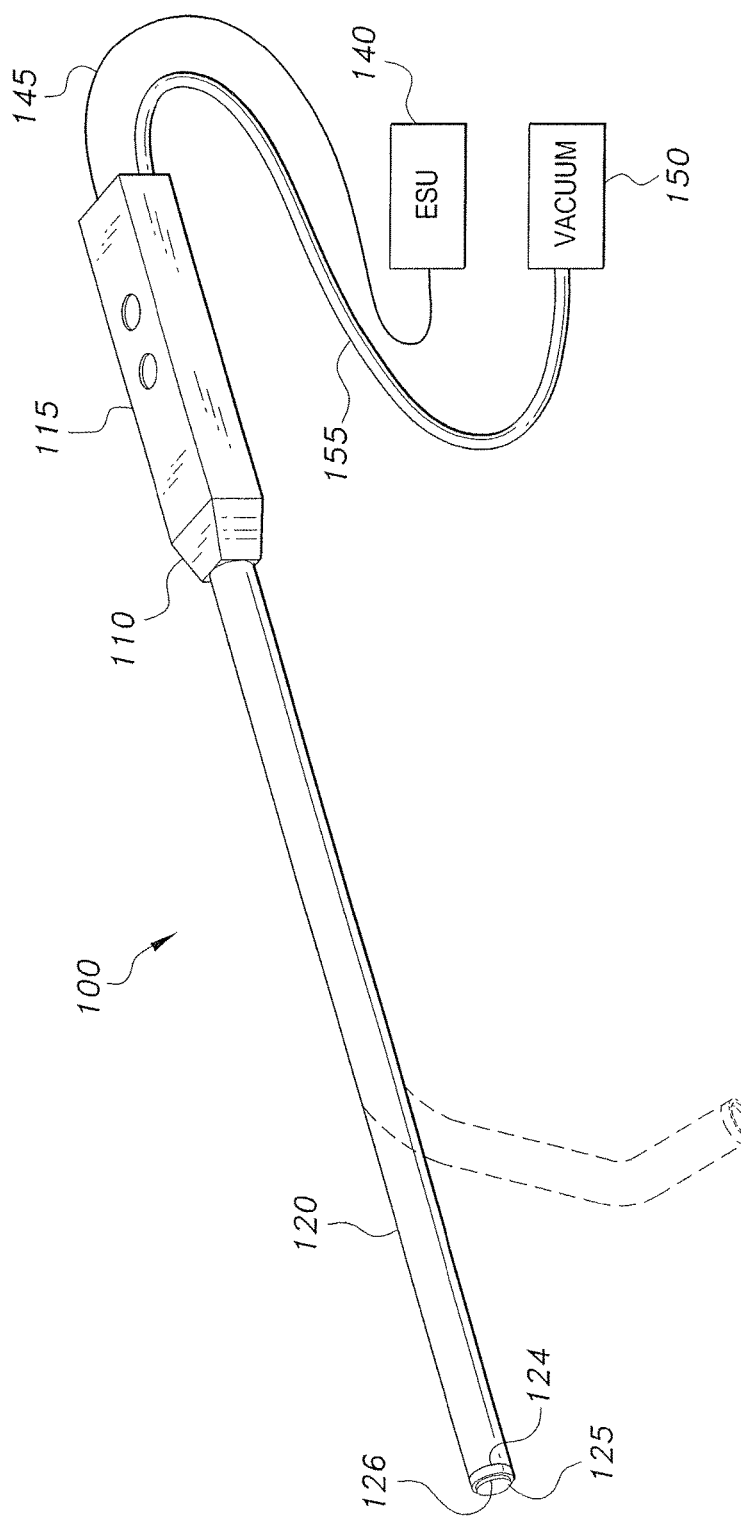
FIG. 2 is a perspective view of a typical prior art electrosurgical suction coagulator.

Referring now to FIGS. 1A and 1B, the shield for an electrosurgical suction coagulator 10 includes a cylindrical cuff 12 and a shielding portion 14. The cylindrical cuff 12 is sized for releasably engaging a distal end 124 of a shaft 120 of an electrosurgical suction coagulator 100, such as the conventional electrosurgical suction coagulator described above with reference to FIG. 2. Shields 10 may be manufactured in a variety of different sizes such that cylindrical cuff 12 may mate with a variety of electrosurgical suction coagulators manufactured with differing shaft diameters. Cylindrical cuff 12 is preferably sized for secure, releasable frictional engagement with the distal end 124 of shaft 120, although it should be understood that any suitable type of securement may be used, such as threaded engagement between cuff 12 and shaft 120, or the like.

The shielding portion 14 is mounted on the cylindrical cuff 12 such that the shielding portion 14 extends distally therefrom. The shielding portion 14 can have an arcuate cross-sectional contour. The shielding portion 14 can have a radius of curvature that is equal to a radius of curvature of the cylindrical cuff 12 and is positioned coaxially therewith. As shown, the shielding portion can form a portion of a cylindrical shell with a radius equal to that of cylindrical cuff 12. The cylindrical cuff 12 and the shielding portion 14 are preferably manufactured as an integral, one-piece unit, and are preferably formed from thermally and electrically insulating material. Thus, when the electrosurgical suction coagulator 100 is in use on a patient's tissue, the shielding portion 14 of shield 10 prevents unintended electrical, electromagnetic or thermal damage to adjacent tissue.

Figure 3:
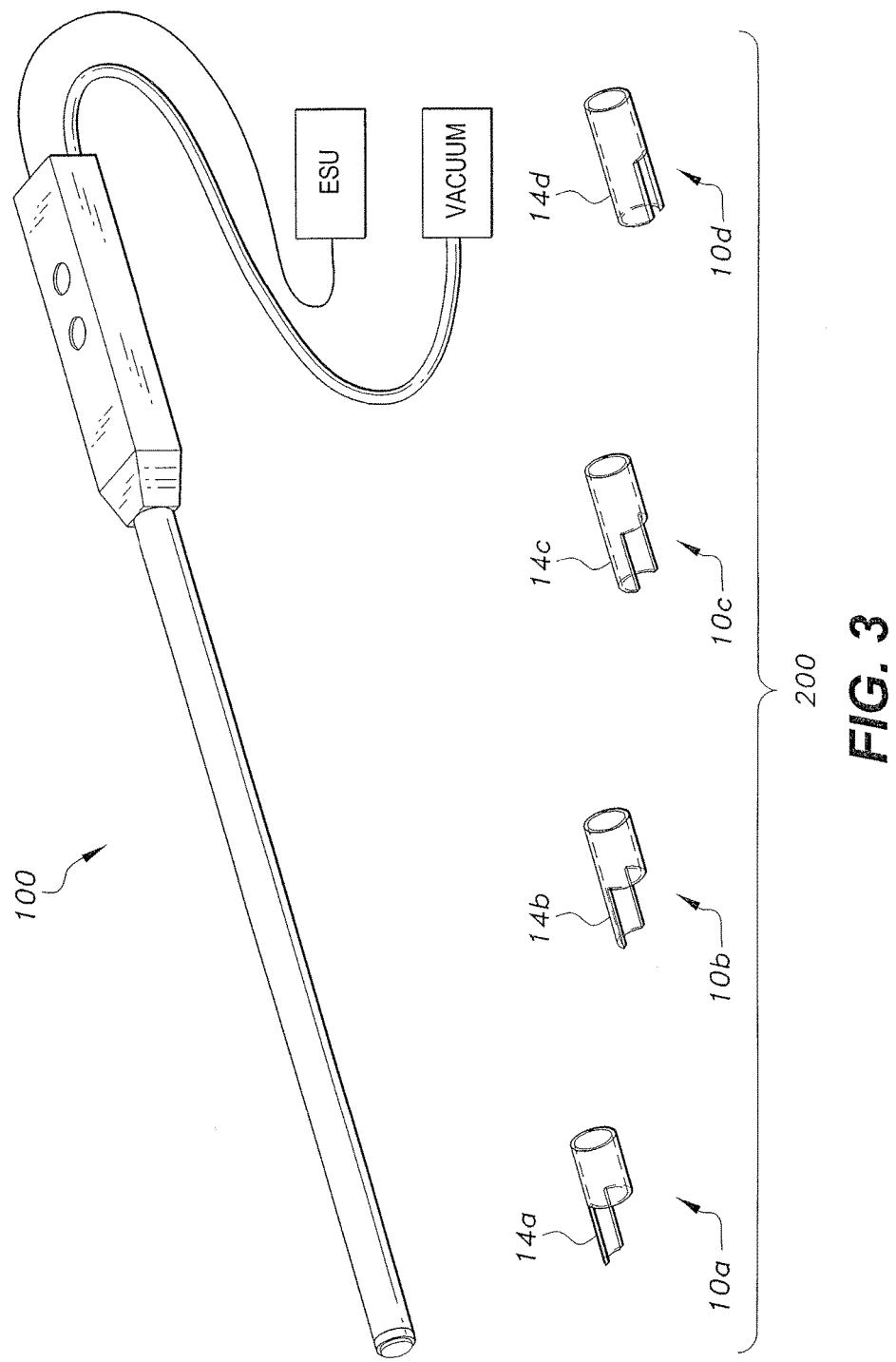
FIG. 3 illustrates a kit including an electrosurgical suction coagulator and a plurality of shields therefor.

As shown in FIG. 3, a plurality of shields 10A, 10B, 10C, 10D for the electrosurgical suction coagulator 100 may be provided in a kit 200 (along with the electrosurgical suction coagulator 100). In the kit 200, a circumferential length of each shielding portion 14A, 14B, 14C, 14D of each shield 10A, 10B, 10C, 10D can be unique, such that a user of the electrosurgical suction coagulator 100 may select a desired one of shields 10A, 10B, 10C, 10D for a desired amount of shielding coverage. For example, shielding portion 14A of shield 10A may span 60° of arc, shielding portion 14B of shield 10B may span 180° of arc, shielding portion 14C of shield 10C may span 210° of arc, and shielding portion 14D of shield 10D may span 240° of arc. It should be understood that the circumferential lengths of shielding portion 14A, 14B, 14C, 14D of each shield 10A, 10B, 10C, 10D are shown in FIG. 3 for exemplary purposes only. Additionally, any desired number of shields may be provided in kit 200.

It is to be understood that the shield for an electrosurgical suction coagulator and the kit including the same are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An electrosurgical suction coagulator kit, comprising:
an electrosurgical suction coagulator, the electrosurgical suction coagulator having a handle at its proximal end and an elongated flexible shaft extending distally from the handle, the distal end of the shaft including an exposed tubular electrode adapted to deliver electrosurgical energy to a patient's tissue, wherein the tubular electrode includes a conduit extending longitudinally therethrough adapted to provide suction to the surgical site; and
a plurality of shields for the electrosurgical suction coagulator, wherein each said shield consists of:
a cylindrical cuff configured for releasably engaging the entire exposed tubular electrode of the distal end of the shaft of the electrosurgical suction coagulator; and
a shielding portion extending from a distal end of said cylindrical cuff, the shielding portion having an arcuate cross-sectional contour, the shielding portion having a radius of curvature equal to a radius of curvature of said cylindrical cuff and being positioned coaxially therewith, wherein the cylindrical cuff and shielding portion each have an imperforate outer surface,
further wherein a circumferential length of each said shielding portion of each said shield is unique and subtends a different constant, uniform arcuate extent from the cuff to the end of the shielding portion such that a desired amount of shielding coverage is achieved, wherein the different arcs are at least 60°, 180°, 210°, and 240°.

2. The electrosurgical suction coagulator kit as recited in claim 1, wherein each said cylindrical cuff and each said shielding portion of each said shield are each formed from an electrically and thermally insulating material.

3. The electrosurgical suction coagulator kit as recited in claim 1, wherein each said cylindrical cuff and each said shielding portion define an integral, one-piece unit.

* * * * *